United States Patent
Nurok et al.

(10) Patent No.: US 7,279,105 B2
(45) Date of Patent: Oct. 9, 2007

(54) ARRANGEMENT AND METHOD FOR PERFORMING CHROMATOGRAPHY

(75) Inventors: David Nurok, Indianapolis, IN (US); Megan Frost, Ann Arbor, MI (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 12 days.

(21) Appl. No.: 10/646,125

(22) Filed: Aug. 22, 2003

(65) Prior Publication Data

US 2004/0050763 A1  Mar. 18, 2004

Related U.S. Application Data

(60) Division of application No. 09/941,205, filed on Aug. 28, 2001, now Pat. No. 6,610,202, which is a continuation of application No. 09/426,297, filed on Oct. 25, 1999, now Pat. No. 6,303,029.

(51) Int. Cl.
B01D 15/08 (2006.01)

(52) U.S. Cl. .................. 210/658; 210/748; 210/198.3; 210/243; 204/450

(58) Field of Classification Search ............... 210/658, 210/748, 198.3, 243; 204/600, 450; 436/162; 422/70
See application file for complete search history.

(56) References Cited

U.S. PATENT DOCUMENTS

| | | |
|---|---|---|
| 3,864,250 A | 2/1975 | Perry |
| 4,346,001 A | 8/1982 | Tyihak |
| 4,438,205 A | 3/1984 | Saint Leger |
| 4,591,524 A | 5/1986 | Tyihak |
| 4,671,870 A | 6/1987 | Tompa |
| 4,671,871 A | 6/1987 | Szekely |
| 4,708,782 A | 11/1987 | Andersen |
| 4,740,298 A | 4/1988 | Andersen |
| 4,865,729 A | 9/1989 | Saxena |

(Continued)

OTHER PUBLICATIONS

Two Records from Dialog regarding Nurok (Journal of Planar Chromatography, vol. 11, Jul./Aug. 1998, pp. 244-246), two pages.*

(Continued)

*Primary Examiner*—Ernest G. Therkorn
(74) *Attorney, Agent, or Firm*—Barnes & Thornburg LLP

(57) ABSTRACT

An arrangement for performing chromatography with a mobile phase and a chromatographic bed having a stationary phase is provided. The arrangement includes a support assembly configured to support the stationary phase. The support assembly has a sealed cavity configured so that when the support assembly is supporting the stationary phase a portion of the chromatographic bed and the stationary phase extends into the sealed cavity. The arrangement further includes a bladder having a void defined therein. The bladder is positioned within the sealed cavity. The arrangement also includes a fluid positioned within the void of the bladder so that the bladder is urged toward the stationary phase within the sealed cavity. The arrangement further includes an anode positioned in contact with the mobile phase. The arrangement also includes a cathode positioned in contact with the stationary phase, wherein creating an electrical potential between the anode and the cathode causes the mobile phase to be advanced through the chromatographic bed positioned within the sealed cavity. An associated method is also provided.

12 Claims, 10 Drawing Sheets

U.S. PATENT DOCUMENTS 5,248,426 A * 9/1993 Stillian et al. .............. 210/635
5,350,510 A    9/1994 Partney

OTHER PUBLICATIONS

*Conference Report*; Journal of Planar Chromatography, 1993; 355-356; Authored by Ian Davies.
*Electroosmotically driven thin-layer electrochromatography on silica media*; 1999; J. Chromatogr. 844; 333-340; Authored by Howard et al.
*Evaporation-induced solvent migration in electrically-driven thin layer chromatography*; 1999, J. Chromatogr. 841; 127-132; Authored by Shafik et al.
*Electro-osmosis: A new concept for high-speed liquid chromatography*; Journal of Chromatography; 1974; 99; 23-30; Authored by Pretorius et al.
*Planar Electrochromatography on non-wetted thin-layers*; Chromatographia; Jan. 1994; vol. 38, No. 1/2; 83-87; Authored by Pukl et al.
*Planar Electrophoresis and Electrochromatography: Time to Revisit these Techniques?*; Journal of Planar Chromatography; Sep./Oct. 97; vol. 10; 332-335; Authored by Poole et al.
*Electrokinetic Ultrafiltration Analysis of Polysaccharides: A new Approach to the Chromatography of Large Molecules*; International Congress on Analytical Chemistry; Jun. 3, 1952; 964-969; Authored by D. L. Mould and R. L. M. Synge.
*Separations of Polysaccharides related to Starch by Electrokinetic Ultrafiltration in Collodin Membranes*; The Rowett Research Institute, Bucksburn, Aberdeenshire; Apr. 15, 1954; 571-585; Authored by D. L. Mould and R. L. M. Synge.
D. Nurok et al., "The Performance of Planar Chromatography using Electroosmotic Flow", *Journal of Planar Chromatography*, vol. 11, Jul./Aug. 1998, pp. 244-246.
D. Nurock et al., "Separation Using Planar Chromatography with Electroosmotic Flow", *Journal of Chromatography A*, 903, 2000, pp. 211-217.
D. Nurock et al., "Variables that Affect Performance in Planar Chromatography with Electroosmotic Flow", *Journal of Planar Chromatography*, vol. 14, Nov./Dec. 2001, pp. 409-414.
D. Nurock et al., "The Performance of Planar Electrochromatography in Horizontal Chamber", *Journal of Planar Chromatography*, vol. 15, Sep./Oct. 2002, pp. 320-323.
D. Nurock et al., "Role of Buffer Concentration and Applied Voltage in Obtaining a Good Separation in Planar Electrochromatography", *Journal of Chromatrography A*, 983, 2003, pp. 247-253.

T. H. Dzido et al., "Planar Electromatography in Horizontal Chamber with Cooling of the Chromatographic Plate", *Proc. International Symposium on Planar Separations*, Budapest, 2003, pp. 129-138.
T. Dzido et al., "Application of a Horizontal DS Chamber to Planar Electrochromatography", *Journal of Planar Chromatography*, vol. 16, May/Jun. 2003, pp. 176-182.
I. Malinowska et al., "Planar Electrochromatography on Silica and Alumina", *Journal of Planar Chromatography*, vol. 11, Nov./Dec. 1998, pp. 411-416.
I. Malinowska, The Inlfuence of Electric Fields on the Chromatographic Process in TLC, *Journal of Planar Chromatography*, vol. 12, Nov./Dec. 1999, pp. 408-415.
I. Malinowska, "Planar Electrochromatogrphy on Nonwetted Layers with Binary Mobile Phases", *Journal of Planar Chromatography*, vol. 13, Jul./Aug. 2000, pp. 307-313.
I. Malinowska, "Some Aspects of the Effect of an Electric Field in Reversed-Phase Thin-Layer Chromatography", *ACTA Chromatographica*, No. 11, 2001, pp. 204-214.
I. Malinowska et al., "The Effect of Electric Fields on Solute Migration and Mixture Separation in TLC", *Journal of Planar Chromatography*, vol. 15, Nov./Dec. 2002, pp. 418-424.
V. Coman et al., "Planar Dielectrochromatogrphy—A Perspective Technique", *Journal of Planar Chromatography*, vol. 16, Sep./Oct. 2003, pp. 338-346.
S. Kreibik et al., "Horizontal Planar Dielectrochromatography. I. Preliminary Results", *Journal of Planar Chromatography*, vol. 15, Nov./Dec. 2002, pp. 425-428.
J. K. Różlo et al., "10 Electroosmotically driven TLC—in Planar Chromatography: A Retrospective View for the Third Millennium, Nyiredy, SZ. ed.", *Springer Scientific*, Budapest, Hungry, 2001, pp. 200-219.
R. Consden et al., "Ionophoresis in Silica Jelly—A Method for the Separation of Amino-Acids and Peptides", *Biochem. J.*, vol. 40, 1946, pp. 33-41.
D. Nurock et al., "Apparatus and Initial Results for Pressurized Planar Electrochromatography", *Analytical Chemistry*, vol. 76, No. 6, Mar. 15, 2004, pp. 1690-1695.
J. M. Koers et al., "Performance of Planar Electrochromatography at Elevated Pressure", *Proc. International Symposium on Planar Separations*, Budapest, 2003, pp. 123-128.

* cited by examiner

ARRANGEMENT AND METHOD FOR PERFORMING CHROMATOGRAPHY

CROSS REFERENCE TO RELATED APPLICATIONS

The present application is a division of U.S. patent application Ser. No. 09/941,205, filed on Aug. 28, 2001 now U.S. Pat. No. 6,610,202, which is a continuation of U.S. patent application Ser. No. 09/426,297, filed on Oct. 25, 1999, now U.S. Pat. No. 6,303,029.

BACKGROUND OF THE INVENTION

The present invention generally relates to an arrangement and method for performing chromatography. The present invention particularly relates to an arrangement and method for performing chromatography utilizing electroosmotic flow of a mobile phase.

Multiple techniques have been developed which enable the separation of complex mixtures into their components. Chromatography is one such technique. Chromatography can be described as a separation process based on differences in the rate at which the components of a mixture move through a chromatographic bed under the influence of a mobile phase which moves relative to a chromatographic bed. The chromatographic bed will typically include a plurality of porous or microporous particles, such as bonded $C_{18}$ silica, wherein the collective surface of these particles make up the stationary phase. Several types of chromatography systems have chromatographic bed packed into the interior of a column. Alternatively, the chromatographic bed can be dispersed on a glass plate. An example of a chromatography system that utilizes the chromatographic bed packed into a column is High Performance Liquid Chromatography (hereinafter referred to as HPLC). An example of a chromatography system that utilizes the chromatographic bed dispersed on a glass plate is Thin Layer Chromatography (hereinafter referred to as TLC) or Overpressurized Layer Chromatography (hereinafter referred to as OPLC).

As previously mentioned HPLC involves packing the chromatographic bed within the interior of a column. The mobile phase is then pumped through the column (and thus through the chromatographic bed) at a very high pressure. A sample is then introduced into the chromatographic system and is pumped through the chromatgraphic bed. As the sample is pumped through the chromatographic bed the components of the sample are partitioned between the mobile phase and the stationary phase based upon their differing physical and chemical characteristics. For example, the components of the mixture can be partitioned between the mobile and stationary phases based upon their polarity, charge, and size. Since the components of a mixture will typically differ based upon their polarity, charge, and size they can be separated from each other by advancing them through the chromatographic bed.

HPLC is a very useful chromatographic technique, however it does suffer from several disadvantages. For example, (i) HPLC system can only separate one mixture at a time, (ii) HPLC systems require special pumps and inlet devices to respectively generate and accommodate the high pressures required to perform HPLC, (iii) HPLC columns must be constructed from mechanically strong materials which limits the use of glass columns that are particularly useful for handling many biological samples, (iv) HPLC systems designed for preparative chromatography techniques are very expensive, and (v) detector dead volumes must be keep extremely small (several microlitres) in order to avoid additional band spreading.

With respect to TLC, the chromatographic bed is a layer (0.1-0.5 mm thick) of a sorbent material spread uniformly over the surface of a glass or plastic plate. The mixture to be separated is applied to the chromatographic bed with a micropipette and dried. The TLC plate is then placed in a chamber so that a small portion of the stationary phase is in contact with a mobile phase. The TLC plate is developed by allowing the mobile phase to ascend up the plate by capillary action. The basis for the separation of the mixture into its respective components is the same as discussed above with respect to HPLC, i.e. the components are separated due to their different partitioning between the stationary and mobile phases. This in turn is based upon the differing polarity, charge, and size characteristics of each of the components of the mixture to be separated.

However, like HPLC, TLC also suffers from several significant disadvantages. In particular, the separation efficiency by TLC is limited by the inadequate mobile phase flow under capillary action. This capillary-induced mobile phase flow is neither fast enough nor constant throughout the chromatographic run, and both of these drawbacks tend to decrease the separation efficiency of TLC substantially. Moreover, the relatively slow movement of the mobile phase results in rather long development times.

OPLC attempts to overcome the aforementioned difficulties associated with TLC. This technique forces the mobile phase through the chromatographic bed disposed on the plate by applying high pressure to the mobile phase. This results in a flow rate that can be controlled and remains constant throughout the development of the plate. A consequence of the constant flow rate is that the number of theoretical plates encountered by a solute will increase linearly with increasing migration distance. In addition, the total time of an analysis is substantially decreased because the mobile phase flows faster.

OPLC also suffers from significant drawbacks. In particular, the flow of the mobile phase in OPLC systems is laminar. Laminar flow profile or parabolic flow profile means that throughout the cross-sectional area of the mobile phase within a channel between particles the center portion of the liquid of the mobile phase flows faster than the liquid close to the wall of the channel. The laminar flow profile of OPLC systems results in migration characteristics of the mobile phase being sensitive to the particle size and the particle size distribution of the stationary phase. Having the migration characteristics of the mobile phase sensitive to the particle size and the particle size distribution of the stationary phase can decrease the separation efficiency of OPLC.

What is needed therefore is a chromatographic arrangement and method which overcomes one or more of the aforementioned problems.

SUMMARY OF THE INVENTION

In accordance with one embodiment of the present invention, there is provided an arrangement for performing chromatography with a mobile phase and a chromatographic bed having a stationary phase. The arrangement includes a support assembly configured to support the chromatographic bed and the stationary phase. The support assembly has a sealed cavity configured so that when the support assembly is supporting the stationary phase a portion of the chromatographic bed and the stationary phase extends into the sealed cavity. The support assembly also includes a first electrode positioned in contact with the mobile phase. The arrangement further includes a second electrode positioned in contact with the stationary phase, wherein creating an electrical potential between the first electrode and the second electrode causes the mobile phase to be advanced through the chromatographic bed positioned within the sealed cavity.

Pursuant to another embodiment of the present invention there is provided a method of performing chromatography with a chromatographic bed having a stationary phase. The method includes the steps of (a) positioning the chromatographic bed and the stationary phase within a sealed cavity, (b) placing the stationary phase in contact with a liquid mobile phase while the stationary phase is positioned within the sealed cavity, (c) advancing a fluid into the sealed cavity so that pressure within the sealed cavity is greater than the pressure outside of the sealed cavity, (d) placing a first electrode in contact with the liquid mobile phase, (e) placing a second electrode in contact with the stationary phase, and (f) creating an electrical potential between the first and second electrode so as to cause the liquid mobile phase to be advanced through the chromatographic bed positioned within the sealed cavity.

According to yet another embodiment of the present invention, there is provided an arrangement for performing chromatography with a mobile phase and a chromatographic bed having a stationary phase. The arrangement includes a support assembly configured to support the chromatographic bed and the stationary phase. The support assembly has a sealed cavity configured so that when the support assembly is supporting the stationary phase a portion of the chromatographic bed and the stationary phase extends into the sealed cavity. The arrangement also includes a fluid positioned within the sealed cavity so that (i) the fluid is placed in a heat exchange relationship with the stationary phase and (ii) pressure within the sealed cavity is greater than pressure outside of the sealed cavity. The arrangement further includes (i) an anode positioned in contact with the mobile phase and (ii) a cathode positioned in contact with the stationary phase, wherein creating an electrical potential between the anode and the cathode causes the mobile phase to be advanced through the chromatographic bed positioned within the sealed cavity.

It is therefore an object of the present invention to provide a new and useful an arrangement and method for performing chromatography.

It is another object of the present invention to provide an improved arrangement and method for performing chromatography.

It is still another object of the present invention to provide an arrangement and method for performing chromatography which can simultaneously separate multiple mixtures.

It is moreover an object of the present invention to provide an arrangement and method for performing chromatography which can efficiently separate the components of a mixture.

It is yet another object of the present invention to provide an arrangement and method for performing chromatography which does not require relatively expensive pumps and inlet devices.

It is still another object of the present invention to provide an arrangement and method for performing chromatography which requires relatively short development times.

It is yet another objective of the present invention to have the mobile phase at optimum velocity for maximum chromatographic efficiency.

The above and other objects, features, and advantages of the present invention will become apparent from the following description and attached drawings.

DETAILED DESCRIPTION OF THE PREFERRED EMBODIMENT

Figure 1:
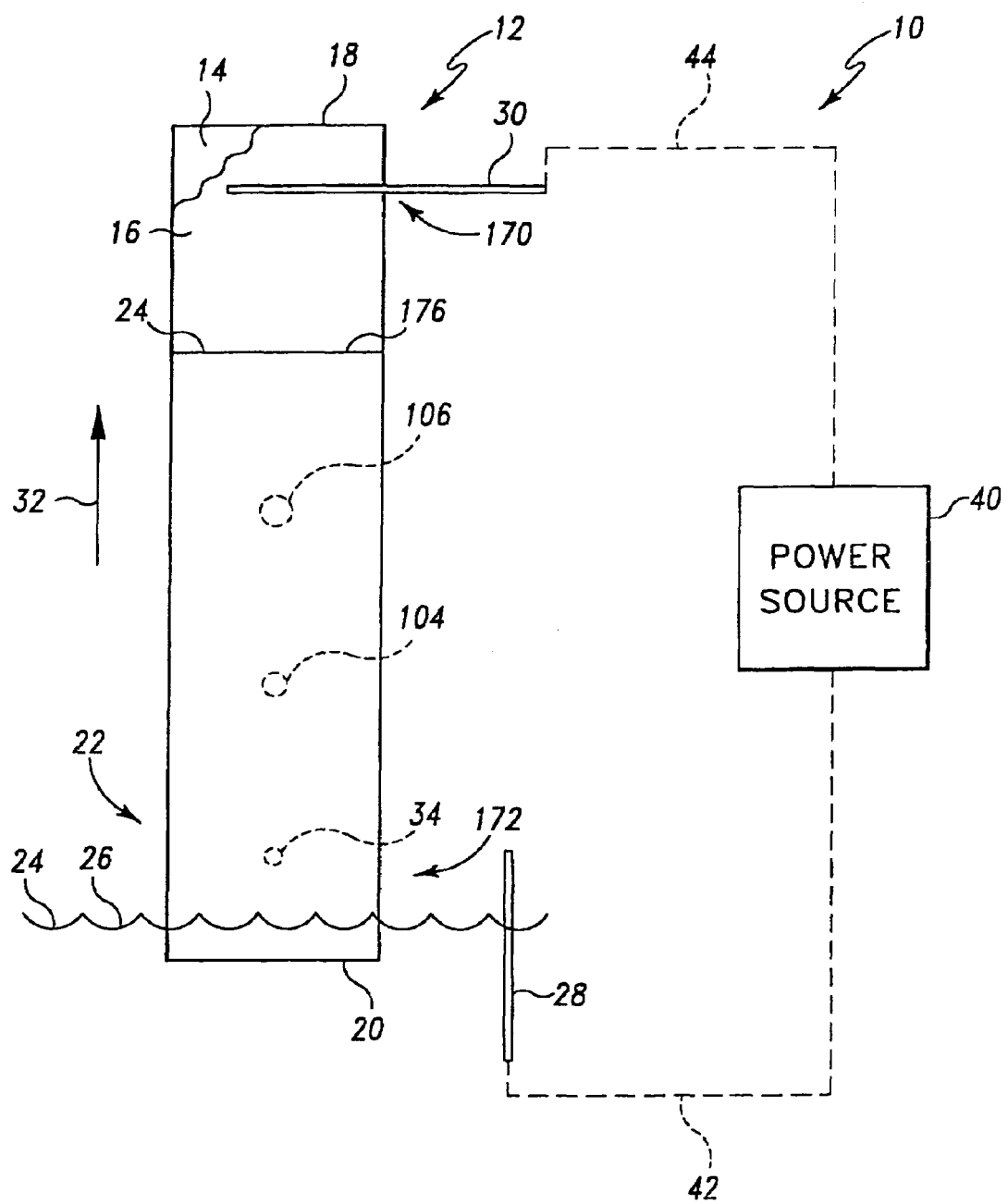
FIG. 1 is an exemplary schematic representation of a chromatography arrangement which incorporates certain features of the present invention therein.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications; equivalents, and alternatives falling within the spirit and scope of the invention as defined by the appended claims.

Referring to FIG. 1 there is shown a chromatography arrangement 10 which incorporates certain features of the present invention therein. Arrangement 10 includes a thin layer chromatography plate 12 (hereinafter referred to as plate 12), an electrical power source 40, a first electrode 28 such as an anode, and a second electrode 30 such as a cathode. Arrangement 10 also includes a mobile phase 24 and a pair of electrical wires 42 and 44. Hereinafter first electrode 28 will be referred to as anode 28 and second electrode 30 will be referred to cathode 30. However, it should be understood that a chromatography arrangement where first electrode 28 is a cathode and second electrode 30 is an anode is also contemplated whereby the chemistry of stationary layer 16 is appropriately altered to accommodate the above described change in the positions of first electrode 28 and second electrode 30.

Plate 12 includes support plate 14 such as a glass or plastic plate. Plate 12 also includes a chromatographic bed 16 disposed and adhered onto a surface of support plate 14 in a well known manner. Plate 12 also includes a cathode portion 170, an anode portion 172, a sample area 22, an end 18, and an end 20. An example of a chromatographic bed 16 which can be used in the present invention is silica gel having a uniform particle size. In particular, the particle size of the silica gel can be from about 2 micrometers to about 10 micrometers. However, it should be understood that the size distribution of the particles should be as narrow as possible. Moreover, the thickness of the chromatographic bed 16 disposed onto the surface of support plate 14 can be from about 0.1 millimeters to about 0.25 millimeters thick. However, thicker stationary phases 16 can be used when performing preparative chromatography. Plates 12 which satisfy the aforementioned criteria and can be used in the present invention are commercially available as catalogue number 15389 (RP-18 $F_{254s}$ plates; note that chromatographic bed of RP-18 is made up of modified silica) from Merck, which: is located in Darmstadt, Germany. Preferably, the aforementioned commercially available plates 12 are conditioned at 120° C. for 20 minutes prior to use in the present invention.

Mobile phase 24 is preferably a liquid. An example of a mobile phase which can be utilized in the present invention is 80% ethanol/water (v/v) with a final {3-[tris(hydroxymethyl amino]-1-propanesulfonic acid} (herein after referred to as TAPS) buffer concentration of about 0.5 mmol to about 2.5 mmol. TAPS is commercially available as catalogue number 21,993-2 from the Aldrich Chemical Company, which is located in Milwaukee, Wis.

All of plate 12 is pre-wetted, except sample area 22, by dipping plate 12 in an aqueous solution whose buffer concentration matched that of the mobile phase 24. Excess liquid is removed by blotting chromatographic bed 16 of plate 12 on a paper towel. A sample mixture to be separated is spotted onto sample area 22 with a micropipette (not shown), a microliter syringe (not shown), or any other appropriate spotting devices prior to pre-wetting the plate 12. Note that the volume of the sample mixture was less that 0.1 microliters. Preferably; the initial spot containing the sample mixture placed onto sample area 22 of plate 12 should be kept as small as possible. In addition, the initial spot is preferably positioned to within 2 millimeters of the pre-wetted portion of plate 12. Note that spot 34, representing the initial spot of the sample mixture to be separated, is shown enlarged for clarity of description.

Figure 3:
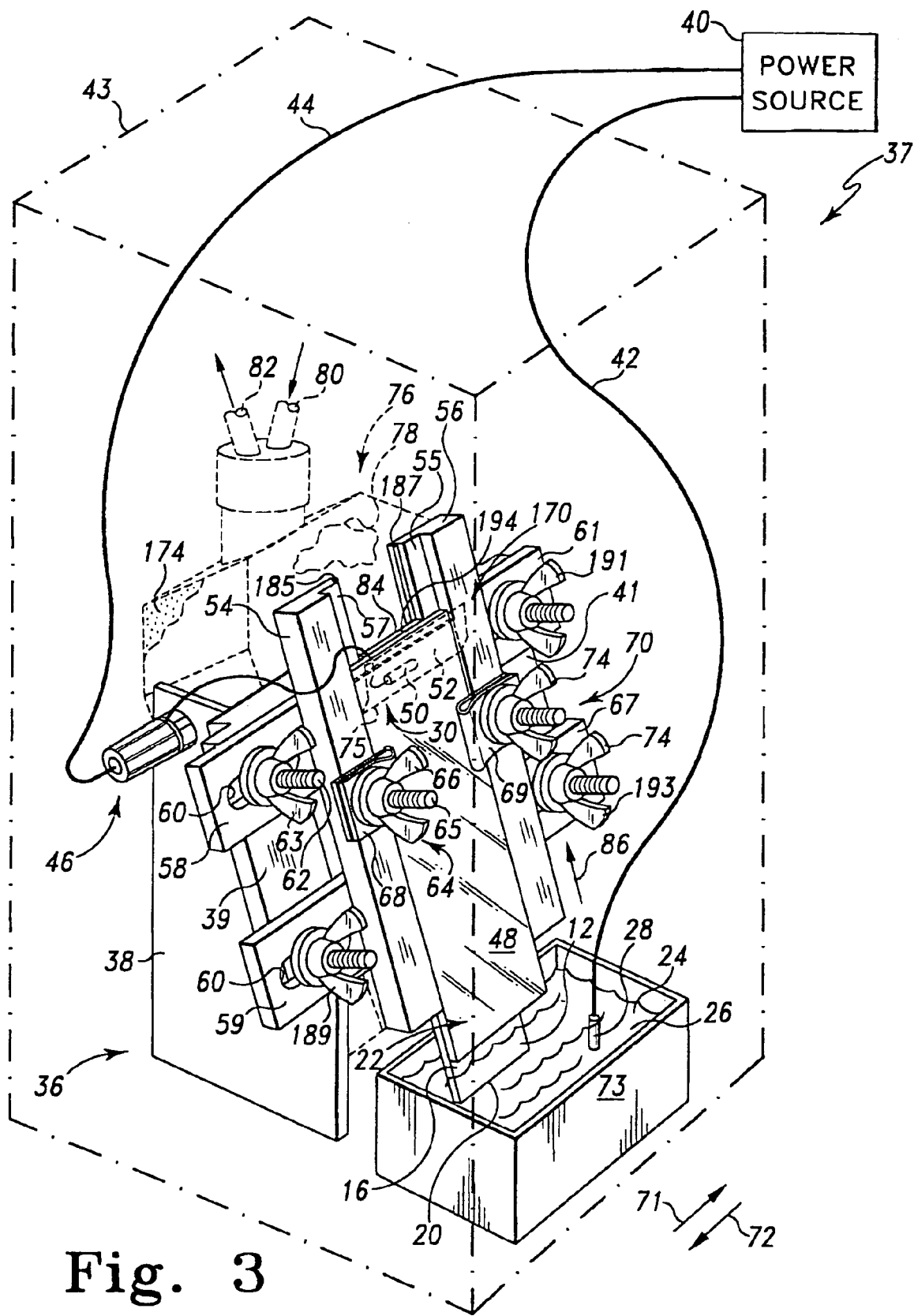
FIG. 3 is perspective view of another chromatography arrangement which incorporates certain features of the present invention therein, note that a housing is shown in phantom for clarity of description.

The plate 12 is positioned relative to the mobile phase 24 such that (i) end 20 of plate 12 is located below the surface 26 of mobile phase 24 and (ii) sample area 22 with spot 34 disposed thereon, is located above the surface 26 of mobile phase 24. It should be understood that a tank can be used to contain mobile phase 24 as shown in FIG. 3.

Anode 28 is electrically coupled to power source 40 via electrical wire 42. In addition, cathode 30 is electrically coupled to power source 40 via electrical wire 44. Anode 28 is placed in contact with mobile phase 24. Cathode 30 is placed into contact with cathode portion 170 of plate 12. Preferably, cathode 30 is urged into direct contact with chromatographic bed 16 with a clamping mechanism, e.g. an electrically non-conducting clamp. Once cathode 30 and anode 28 are positioned as described above and electrically coupled to power source 40 an electrical potential is created between cathode 30 and anode 28 with power source 40. It should be understood that the electrical potential should be created between cathode 30 and anode 28 about 10 seconds to about 30 seconds after end 20 of plate 12 is located below the surface 26 of mobile phase 24.

The magnitude of the electrical potential created with power source 40 is limited by the amount of current the power source 40 can tolerate, and by the ohmic heating which can cause plate 12 to dry out during the development thereof. For example, in the present invention the electrical potential generated by power source 40 can range from about 500 V to about 2500 V. A power source which can be used in the present invention for generating the aforementioned electrical potentials is commercially available from the Spellman High Voltage Electronics. Company, located in Plainview, N.Y., as model SL30P600 or model number SL30N600.

When the aforementioned electrical potential is generated between anode 28 and cathode 30 cations present in the mobile phase 24 are attracted to the negatively charged cathode 30. This migration of cations toward the cathode causes mobile phase 24 to be advanced through the chromatographic bed 16 in the direction indicated by arrow 32, i.e. toward cathode 30. The process of advancing mobile phase 24 through chromatographic bed 16 by placing a first electrode 28 in contact with mobile phase 24 and a second electrode 30 in contact with chromatographic bed 16 and then generating an electrical potential between first electrode 28 and second electrode 30 will hereinafter be referred to as electroosmosis.

As previously discussed, as mobile phase 24 is advanced toward cathode 30 the components of the mixture contained within initial spot 34 partition between mobile phase 24 and chromatographic bed 16 based upon their differing physical and chemical characteristics. Since the components of mixture contained within initial spot 34 will typically differ based upon their polarity, charge, and size they are separated from each other as plate 12 is developed, i.e. as the front 176 of mobile phase 24 is advanced through chromatographic bed 16 away from anode position 172 and toward cathode position 170.

An exemplary separation is depicted in FIG. 1. In particular, the mixture initially disposed onto sample area 22 of plate 12 as spot 34 is depicted as containing two components, i.e. spot 104 and spot 106. As shown in FIG. 1, utilizing chromatography arrangement 10 as described above results in these two components being separated from each other along the longitudinal axis of plate 12. Once separated, spots 104 and 106 can be detected or visualized with various well known techniques. For example, after development and drying, spots 104 and 106 could be visualized by scanning plate 12 with a dual wavelength flying-spot scanner at $\lambda=254$ nm in the reflectance mode. One such scanner which can be used in the present invention is commercially available from the Shimadzu Corporation, located in Kyoto, Japan as model number CS9000U dual wavelength flying-spot scanner.

It should be appreciated that utilizing electroosmosis to advance mobile phase 24 through chromatographic bed 16 has several advantages over advancing a mobile phase through a chromatographic bed with pressure or capillary action. In particular, as shown in FIG. 2A, utilizing electroosmosis to advance mobile phase 24 through chromatographic bed 16 in the direction of arrow 150 results in mobile phase 24 having a plug flow profile 183. Having a plug flow profile results in the cross sectional velocity of the flow of mobile phase 24 being constant. This results in a reduction in transaxial zone broadening, which substantially increases the separation efficiency of chromatography arrangement 10 as compared to other chromatography arrangements which utilize pressure or capillary action to advance the mobile phase through the stationary phase. Specifically, chromatography arrangements which depend upon pressure or capillary action to advance the mobile phase through the chromatographic bed have laminar mobile phase flow profiles (i.e. parabolic flow profiles).

Figure 2B:
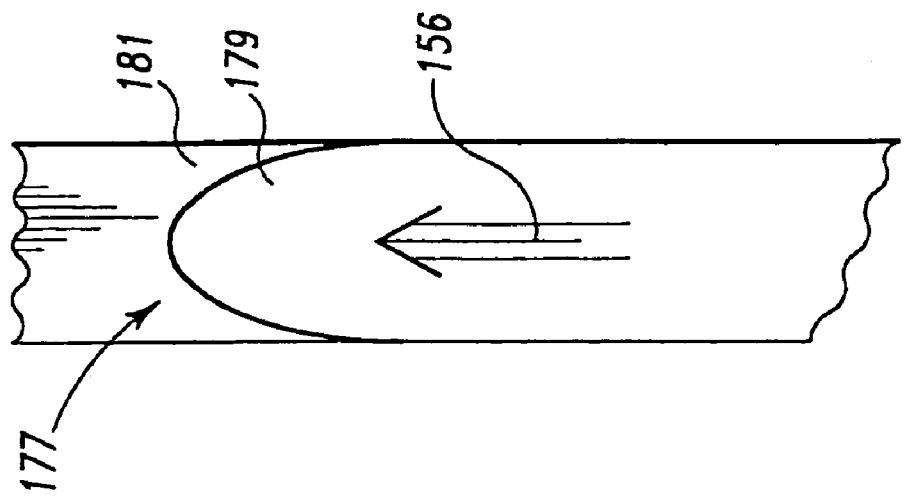
FIG. 2B is a schematic representation of a laminar flow profile (parabolic profile) of the mobile phase obtained with chromatography arrangements such as OPLC.
Figure 2A:
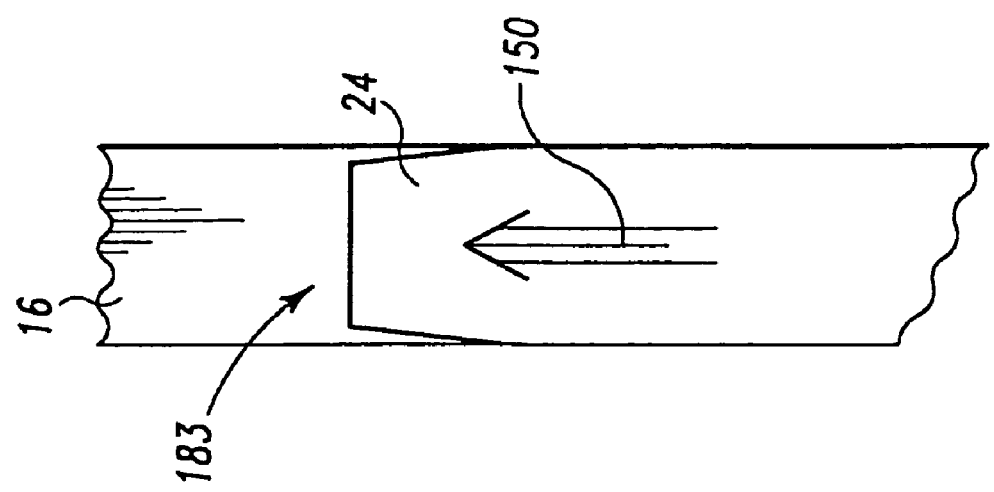
FIG. 2A is a schematic representation of a plug flow profile of the mobile phase obtained with the chromatography arrangements of the present invention.

In particular, in FIG. 2B there is shown a flow profile 177 of a mobile phase 179 being advanced through a chromatographic bed 181 in the direction indicated by arrow 156 with pressure. As previously mentioned, advancing a mobile phase through a chromatographic bed with pressure results in a laminar flow profile. In other words, the center portion of the liquid of mobile phase 179 flows faster than the liquid close to the surface as mobile phase 179 is advanced through chromatographic bed 181. This laminar flow profile increases the transaxial contributions to zone broadening which substantially decreases the separation efficiency of such pressure driven chromatography arrangements. Moreover, having a pressure driven mobile phase results in the migration characteristics of the mobile phase being sensitive to (i) the particle size and (ii) the particle size distribution of the stationary phase. Having the migration characteristics of the mobile phase sensitive to the aforementioned parameters also decreases the separation efficiency of such pressure or capillary action driven mobile phase chromatography arrangements.

Furthermore, utilizing electroosmosis to advance mobile phase 24 through chromatographic bed 16 has several additional advantages over advancing a mobile phase through a chromatographic bed with pressure or capillary action. These advantages include the ability to achieve optimum and constant linear velocity of the mobile phase, and an increased total number of theoretical plates available for separation. Additionally, with electroosmosis the length of the chromatographic bed (e.g. the length of plate 12) will no longer be a limiting factor in gaining greater efficiency because the decrease in linear velocity with distance traveled will no longer be an issue as in capillary mediated chromatography arrangements. In other words their is no theoretical limit to the length the chromatographic bed can be used in this arrangement. Furthermore, the flow rate of the mobile phase in electroosmotic systems is independent of the particle size and packing uniformity of the chromatographic bed which facilitates a greater separation efficiency.

Referring now to FIG. 3, there is shown a chromatography arrangement 37 which is similar to arrangement 10. Arrangement 37 functions in substantially the same way, and has the same advantages, as discussed above in reference to arrangement 10. In particular, it should be understood that arrangement 37 also drives the mobile phase 24 through the chromatographic bed 16 of plate 12 utilizing an electrical potential generated between first electrode 28 and second electrode 30. However, arrangement 37 includes a support assembly 36 for supporting plate 12, and therefore chromatographic bed 16. Arrangement 37 also includes an enclosure 43 which surrounds support assembly 36 and plate 12 when plate 12 is being developed. Enclosure 43 includes a door (not shown) operatively coupled to a safety switch (not shown) which disables power source 40 when the door is opened. In addition, arrangement 37 differs from arrangement 10 in that the cathode 30 of arrangement 37 includes a piece of platinum foil 52 (about 0.8×2 cm) spot welded to a platinum wire 50. Note that the platinum wire 50 shown in FIG. 3 is enlarged for clarity of description. Moreover, arrangement 37 also includes a wick 75 for absorbing the liquid of mobile phase 24. The absorptive capacity of wick 75 can be augmented by a porous bag filled with an absorptive material and then placing the porous bag in intimate contact with wick 75.

Support assembly 36 includes a frame 38, a plate 39, a plate 41 and a tank 73. Support assembly 36 also includes brackets 58, 59, 61, and 67. The aforementioned elements can be made of delrin or Plexiglas. Note that all of the parts that may come into contact with the mobile phase or its vapor should be made out of delrin. Also note that each of brackets 58, 59, 61, and 67 include an elongated slot 60 defined therein. Support assembly 36 also includes clamping member 54 and a clamping member 56. Clamping member 54 has a first notch 57 and a second notch 185 defined therein. In a similar manner, clamping member 56 has a first notch 55 and a second notch 187 defined therein.

Plates 39 and 41 are secured to frame 38 as shown in FIG. 3. Bracket 58 is secured to plate 39 with a screw 62 that extends through elongated slot 60 and a hole (not shown) defined in plate 39. A nut 63 is then meshingly engaged with screw 62 to ensure that bracket 58 remains secured to plate 39 (a washer can also be interposed between nut 63 and bracket 58 if necessary). It should be appreciated that securing bracket 58 to plate 39 in the above described manner allows bracket 58 to move relative to plate 39 in the direction indicated by arrows 71 and 72. However, bracket 58 can be locked into position relative to plate 39 by tightening nut 63. Bracket 59 is secured to plate 39 in a substantially identical manner as that described for bracket 58. Thus, bracket 59 can also be moved relative to plate 39 in the directions indicated by arrows 71 and 72 or locked into position relative to plate 39 by tightening nut. Brackets 61 and 67 are secured to plate 41 in a substantially identical manner as that described for bracket 58. In addition, brackets 61 and 67 function in a substantially identical manner as that described for bracket 58.

Clamping member 54 is secured to brackets 58 and 59 so clamping member 54 can also move relative to plate 39 in the directions indicated by arrows 71 and 72. In a similar manner clamping member 56 is secured to brackets 61 and 67 such that clamping member 56 can move relative to plate 41 in the directions indicated by arrows 71 and 72.

Each clamping member 54 and 56 has a holding mechanism 64 and 70, respectively, attached thereto. Holding mechanism 64 includes a screw 65 extending through clamping member 54. An intermediate member 68 is then disposed over screw 65. A nut 66 is then meshingly engaged with screw 65 so that intermediate member 68 is interposed between nut 66 and clamping member 54. Holding member 70 is attached clamping member 56 in a substantially identical manner as that described for holding member 64.

During use of arrangement 37 plate 12 is pre-wetted as described above. The sample to be separated is then spotted on sample area 22 of plate 12. Plate 12 is then positioned relative to clamp member 54 and clamp member 56 such that (i) one edge of plate 12 is located within second notch 185 of clamping member 54 and (ii) the opposite edge of plate 12 is located within second notch 187 of clamping member 56. Plate 12 further positioned such that end 20 is located below the surface 26 of mobile phase 24. However, sample area 22 should be located above surface 26 of mobile phase 24. Once positioned as described above, clamping members 54 and 56 are gently urged together. Nuts 63, 189, 191, and 193 are then tightened to lock clamping members 54 and 56 in their place.

Platinum foil 52 of cathode 30 is placed into contact with cathode portion 170 of plate 12. Wire 44 is electrically coupled to platinum wire 50 and power source 40. Note that arrangement 37 incorporates a securement mechanism 46 attached to frame 38 for supporting wire 44. As with arrangement 10, anode 28 is placed in contact with mobile phase 24 and electrically coupled to power source 40 with wire 42 so that mobile phase 24 is advanced up plate 12 in the direction indicated by arrow 86.

Figure 7:
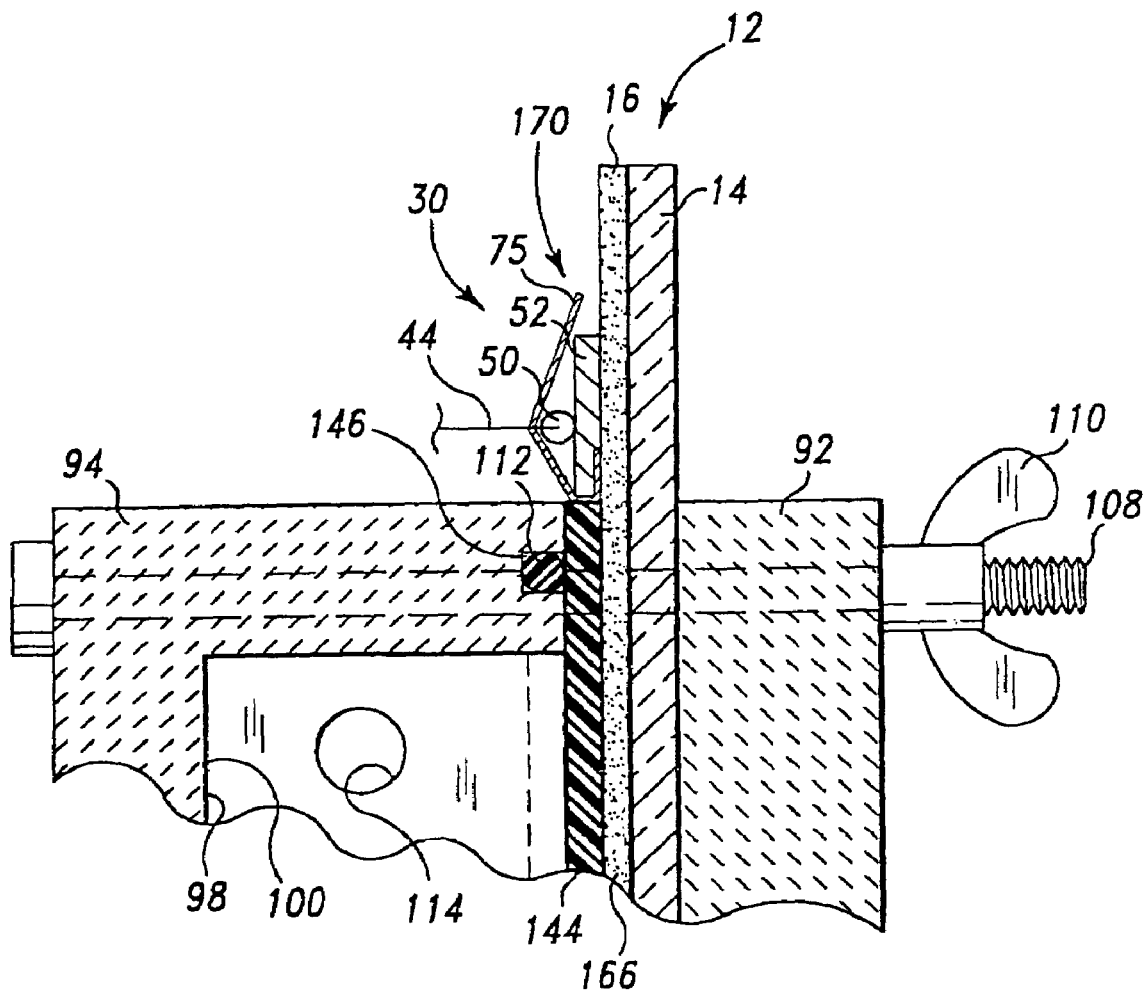
FIG. 7 is an enlarged cross sectional fragmentary view of an upper portion of the chromatography arrangement of FIG. 5 showing the wick and cathode configuration (note that the elements of the cathode are enlarged for clarity of description)

As more clearly shown in FIG. 7, wick 75 is preferably a piece of filter paper. The filter paper is folded along an edge thereof so that a 1-2 mm lip is created. The lip is then positioned underneath a bottom edge of platinum foil 52 so that the lip is interposed between platinum foil 52 and chromatographic bed 16 of plate 12. The remaining portion of wick 75 extends out in front of cathode 30 in an upwardly direction. The length of wick 75 can be increased so that wick 75 extends upwardly for a substantial distance above the end of plate 12. Doing so enhances the absorptive capacity of wick 75.

A glass plate. 48 is disposed over chromatographic bed 16 of plate 12 such that opposing edges of glass plate 48 are located within notches 55 and 57 of clamping members 56 and 54. In addition, a number of spacers (not shown) are interposed between glass plate 48 and plate 12 such that an air gap 194 about ⅛ of an inch wide is created between glass plate 48 and plate 12. Both intermediate members 68 and 69 are disposed around their respective screws (e.g. screw 65). The nuts 66 and 74 of holding members 64 and 70 are tightened such that intermediate members 68 and 69 are urged toward glass plate 48. Urging that intermediate members 68 and 69 toward glass plate 48 holds plate 12 and glass plate 48 interposed between clamping members 54 and 56. Moreover, a small piece of rubber (not shown) is interposed between glass plate 48 and platinum foil 52 so that the rubber piece urges platinum foil 52 against chromatographic bed 16 when intermediate members 68 and 69 are urged against glass plate 48.

A dye mixture was separated utilizing arrangement 37. The dye mixture separated is commercially available from Analtech, located in Newark, N.J., as catalogue number 30-04 (Test Mixture IV). The dye mixture was spotted onto sample area 22 of plate 12. Plate 12 was then prepared as described above and placed into support assembly 36 as previously described for development.

The dye mixture was separated using an electrical potential of 2000 V and a 1.0 mmol TAPS buffer concentration on a plate 12 having the dimensions of 2.5×10.0 cm. The same separation using conventional TLC chromatography was also performed. The development of each plate was terminated when the mobile phase reached 5.5 cm from the bottom edge of the plate. The plate 12 utilizing arrangement 37 developed in 18 min. as compared to 37.5 min. for the plate developed with conventional TLC chromatography.

Figure 9A:
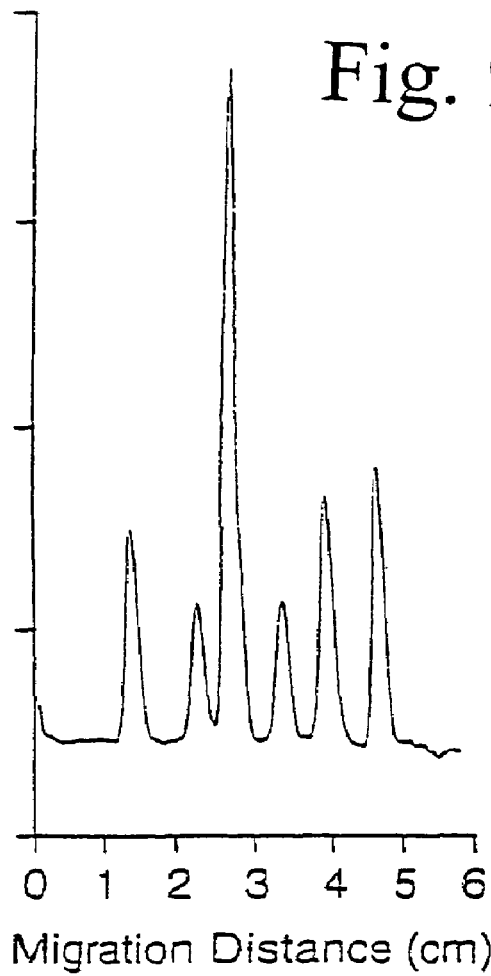
FIG. 9A depicts a chromatogram obtained by the chromatography arrangement shown in FIG. 3 utilizing an 80% aqueous ethanol (v/v) (8 parts ethanol and 2 parts water) mobile phase containing 1 mmol TAPS buffer with an applied electrical potential of 2000 volts.
Figure 9B:
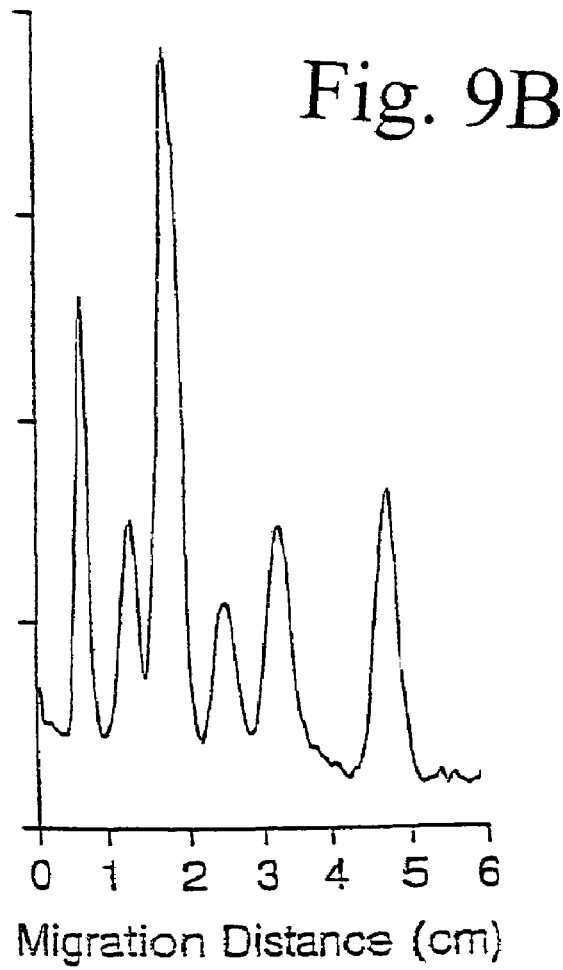
FIG. 9B depicts a chromatogram obtained by conventional TLC utilizing an 80% aqueous ethanol (v/v) mobile phase containing 1 mmol TAPS buffer.

Table 1 sets forth the width of the peaks at half height ($w_{0.5}$), the migration distance (MD), and the number of theoretical plates (N) obtained in each separation. The peaks obtained utilizing arrangement 37 (electroosmosis) are more narrow (0.17 to 0.18 cm) as compared to the conventional TLC chromatography arrangement (0.18 to 0.38 cm). Moreover, the number of theoretical plates utilized was higher by a factor of 2.5 to 4.6 in arrangement 37 as compared to the conventional TLC chromatography arrangement for the same distance traveled. The chromatogram obtained for arrangement 37 and the conventional TLC arrangement is shown in FIGS. 9A and 9B, respectively.

TABLE 1

| | Electroosmosis | | | Conventional TLC Conventional | | |
|---|---|---|---|---|---|---|
| Solute | MD (cm) | $w_{0.5}$ (cm) | N | MD (cm) | $w_{0.5}$ (cm) | N |
| 1 | 1.34 | 0.18 | 325 | 0.60 | 0.18 | 60 |
| 2 | 2.19 | 0.17 | 964 | 1.22 | 0.25 | 132 |
| 3 | 2.61 | 0.17 | 1370 | 1.67 | 0.27 | 218 |
| 4 | 3.22 | 0.18 | 1715 | 2.34 | 0.33 | 274 |
| 5 | 3.79 | 0.17 | 2888 | 3.08 | 0.38 | 374 |
| 6 | 4.49 | 0.18 | 3647 | 4.51 | 0.29 | 1331 |

Figure 11:
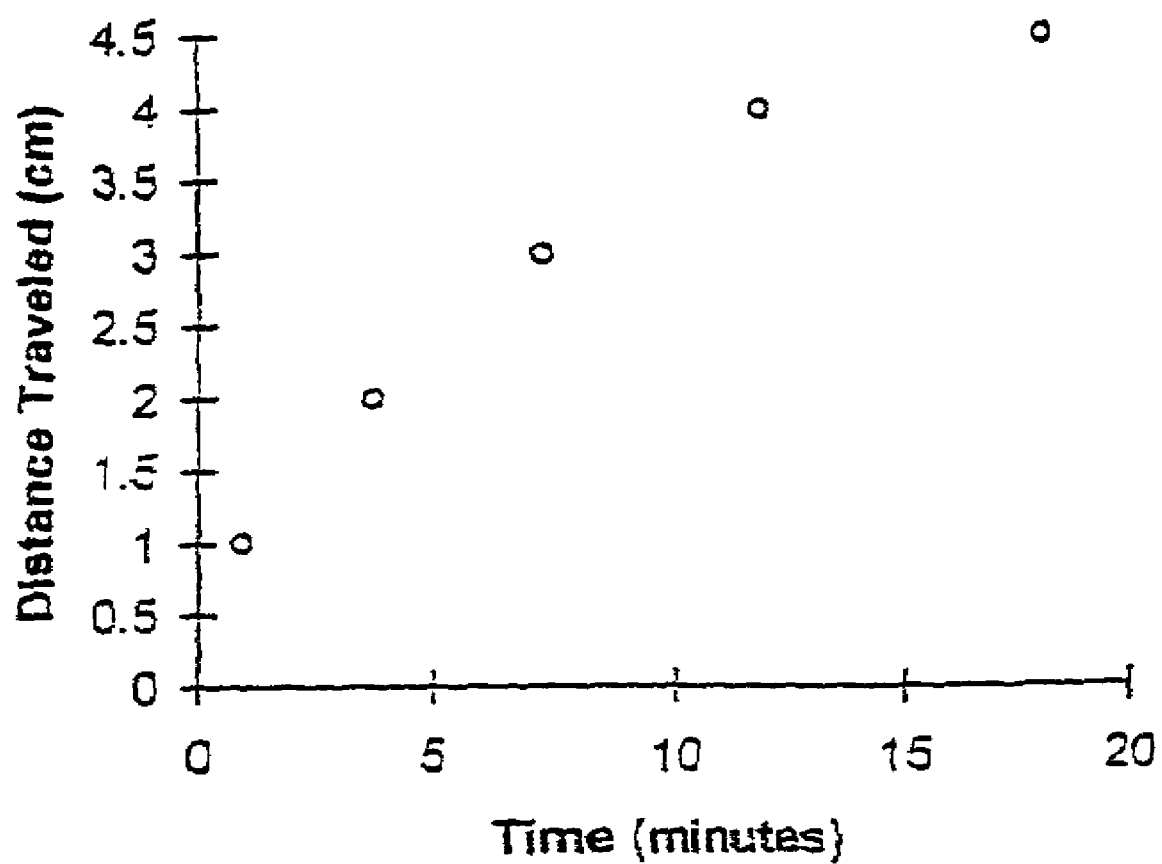
FIG. 11 depicts a graph showing distance traveled and elapsed time for a separation obtained by the chromatography arrangement shown in FIG. 3 utilizing an 80% aqueous ethanol (v/v) mobile phase containing 1 mmol TAPS buffer with an applied electrical potential of 2000 volts.

In addition, the elapsed time and distance traveled of the highest migrating dye component in arrangement 37 is shown in Table 2. These results are graphically shown in FIG. 11.

TABLE 2

| Time (min) | Distance traveled (cm) |
|---|---|
| 0.90 | 1.0 |
| 3.68 | 2.0 |
| 7.31 | 3.0 |
| 11.92 | 4.0 |
| 18.00 | 4.5 |

Figure 10:
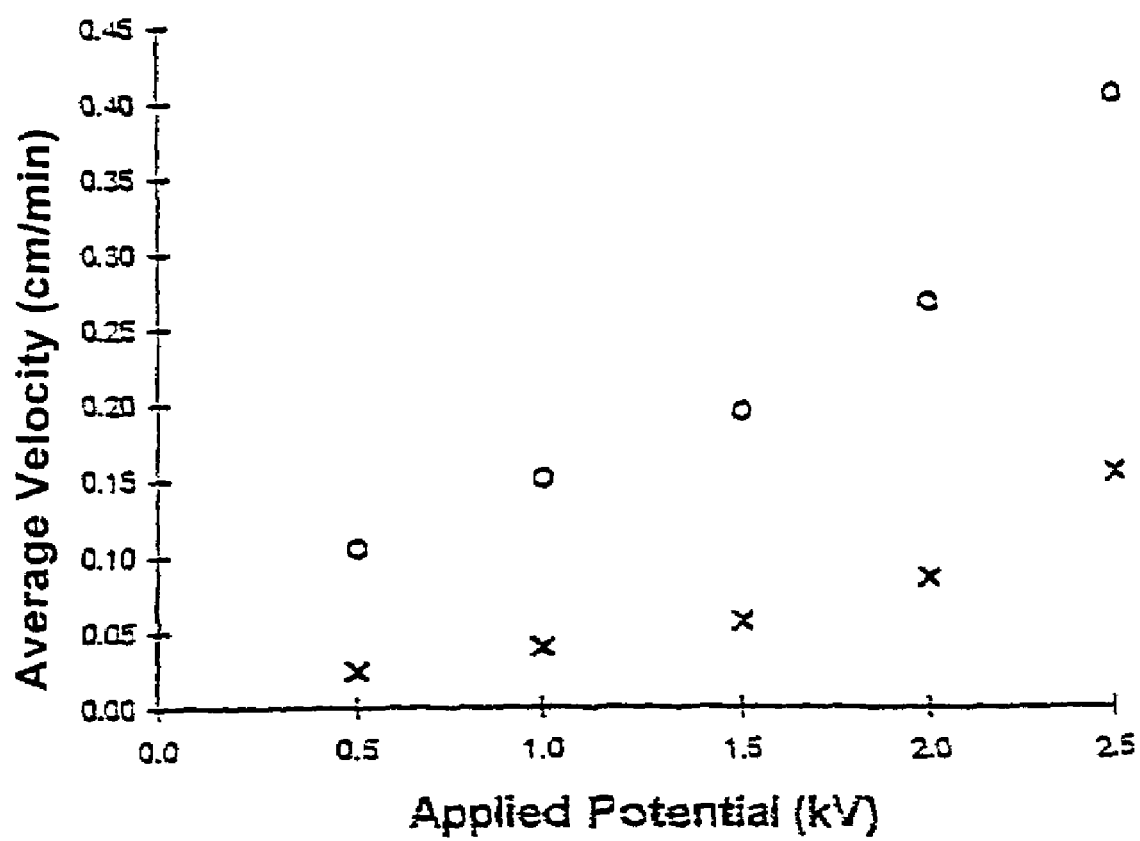
FIG. 10 depicts a graph showing the average velocity of the highest (o) and lowest (x) dye components of a mixture obtained by the applied potential utilizing the chromatography arrangement shown in FIG. 3 with an 80% aqueous ethanol (v/v) mobile phase containing 1 mmol TAPS buffer.

The dye mixture was separated using 1.0 mmol TAPS buffer concentration and an applied potential ranging from 500 V to 2500 V in steps of 500 V. Plates 12 were cut into 2×10 cm sections and then used. However, much larger plates can be utilized. The separation was terminated when the highest migrating dye component traveled 5 cm from the bottom edge of the plate 12. Table 3 lists the applied potential, time required for the separation, and the average velocity of the highest and lowest migrating dye components. FIG. 10 is a plot of the average velocity vs. applied potential. The average velocity increases with increasing applied potential. The highest potential applied is limited by the amount of current the power supply can tolerate, and by ohmic heating causing plate 12 to dry. The plates 12 used in the subject voltage study were slightly more narrow than those previously used (2 cm as compared to 2.5 cm). This allows a slightly higher potential to be applied without the current exceeding the limitations of the power source.

TABLE 3

| Applied potential (kV) | Total time of development (min) | Average velocity of highest spot (cm/min) | Average velocity of lowest spot (cm/min) |
|---|---|---|---|
| 0.5 | 37.82 | 0.105 | 0.024 |
| 1.0 | 26.10 | 0.151 | 0.040 |
| 1.5 | 20.25 | 0.194 | 0.057 |

TABLE 3-continued

| Applied potential (kV) | Total time of development (min) | Average velocity of highest spot (cm/min) | Average velocity of lowest spot (cm/min) |
| --- | --- | --- | --- |
| 2.0 | 14.33 | 0.267 | 0.086 |
| 2.5 | 9.95 | 0.402 | 0.154 |

Still referring to FIG. 3, there is shown a housing 76 which can be used in conjunction with frame 38 of assembly 37. Housing 76 has an interior chamber 78 defined therein. Housing 76 is also equipped with an entrance port 80 and an exit port 82. Both entrance port 80 and exit port 82 are in fluid communication with interior chamber 78.

When housing 76 is used in conjunction with arrangement 37, housing 76 is positioned relative to frame 38 so that it is located adjacent to a back surface of plate 12. In particular, housing 76 is located adjacent to the back surface of plate 12 so that a space 84 is defined between housing 76 and the back surface of plate 12 (about 1/16 of an inch separation between housing 76 and plate 12). Entrance port 80 is then placed in fluid communication with a pump (not shown) for advancing a cooling fluid 174 through interior cavity 78. Specifically, the pump circulates cooling fluid 174 through interior chamber 78 of housing 76 via entrance port 80 and exit port 80 during the development of plate 12.

Having housing 76 positioned relative to plate 12 in the aforementioned manner is an advantage, in that cooling fluid 174 facilitates keeping the temperature of plate 12 within an acceptable range during the development of plate 12. Specifically, cooling fluid prevents plate 12 from becoming over heated during the development of plate 12 and thus enhances the separation efficiency of arrangement 37.

Now referring to FIGS. 4, 5, 6, and 7, there is shown a chromatography arrangement 88 which is similar to arrangement 37. Arrangement 88 functions in substantially the same way, and has the same advantages, as discussed above in reference to arrangement 37. In particular, it should be understood that arrangement 88 also drives the mobile phase 24 through the chromatographic bed 16 of plate 12 utilizing an electrical potential generated between first electrode 28 and second electrode 30. However, support assembly 36 of arrangement 88 includes a container 90 for enclosing a portion 166 of chromatographic bed in a sealed cavity 100. Arrangement 88 also includes a temperature control unit 128, a pump 122, a cooling unit 132, and a temperature sensor 126.

Container 90 includes a first member 92 and a second member 94. First member 92 and second member 94 are preferably constructed from a non-electrically conducting ceramic material encased in polycarbonate (Lexan). Polycarbonate which can be utilized in the present invention to encase the ceramic material is commercially available from the McMaster-Carr Supply Company located in Chicago, Ill.

Figure 4:
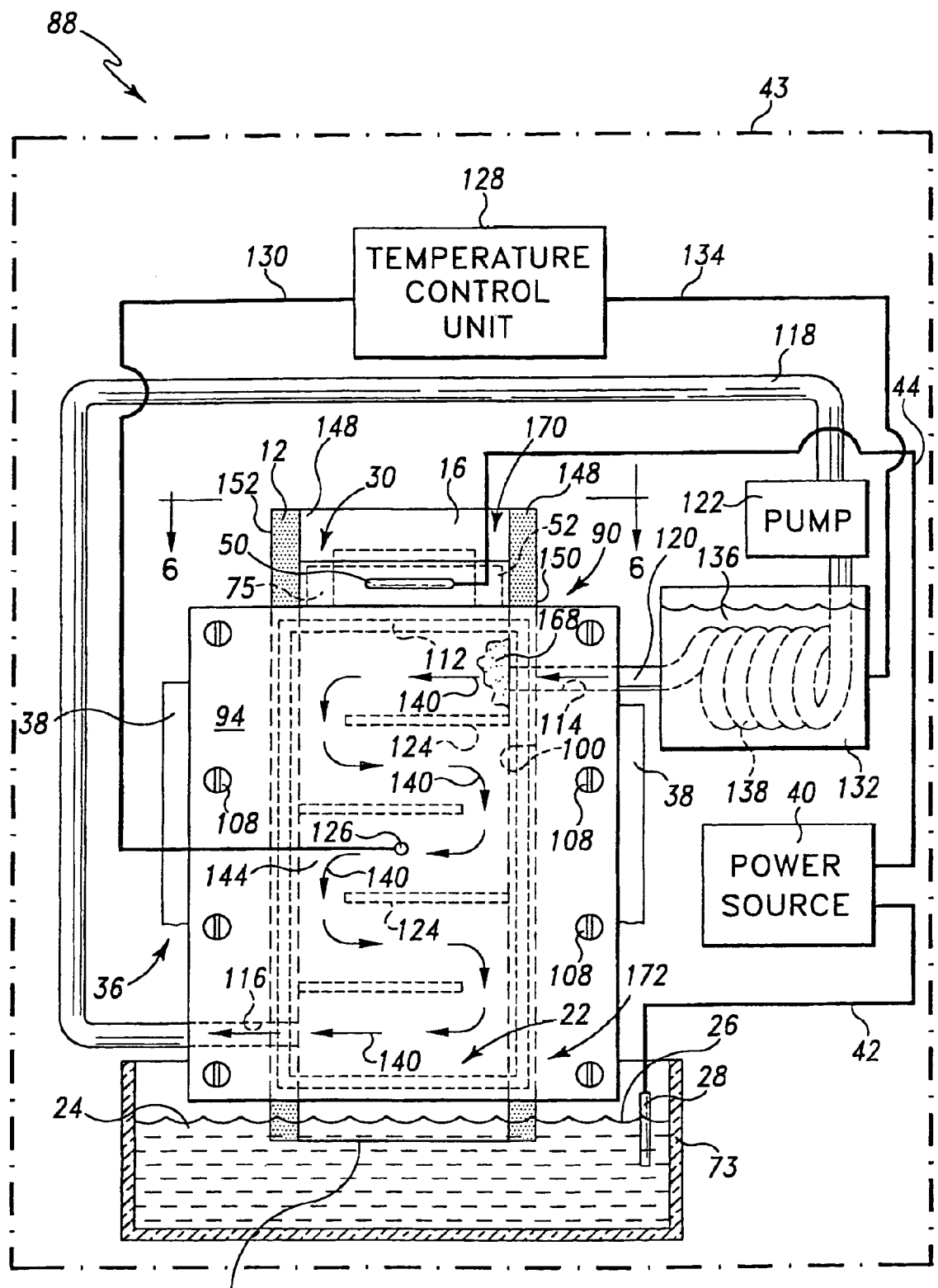
FIG. 4 is partially schematic front elevational view of another chromatography arrangement which incorporates certain features of the present invention therein.
Figure 5:
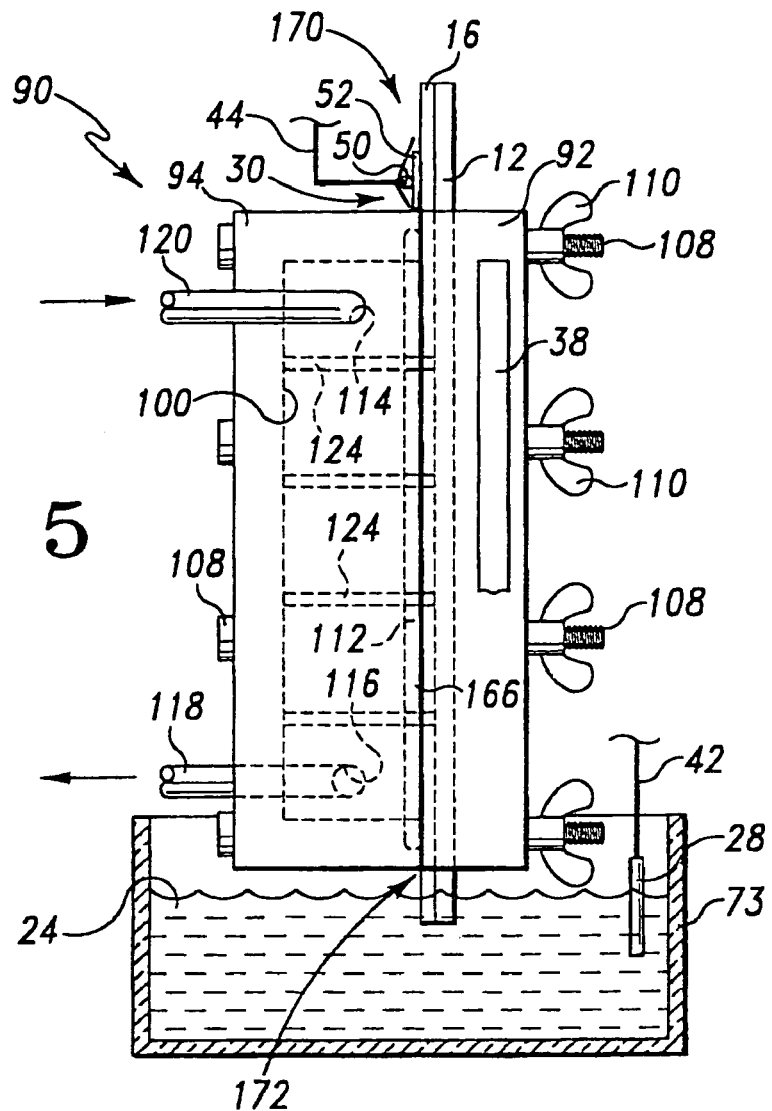
FIG. 5 is a partially schematic side elevational view of the arrangement shown in FIG. 4.

First member 96 has a seat area 96 and a number of holes 102 (see FIG. 6) defined therein. First member 92 is secured to frame 38 so that first member 92 can be held in an upright position as shown in FIGS. 4 and 5. Second member 94 has cut out portion 98 and a number of holes 102 (see FIG. 6) defined therein. In addition, second member 94 has a channel 146 defined therein as shown in FIG. 7. A gasket 112 is positioned within channel 146.

When using arrangement 88 to perform chromatography, plate 12 is first pre-wetted as described above. In addition, edges 150 and 152 of plate 12 are coated with a sealant 148 as shown in FIG. 4. The sealant 148 can be an epoxy based resin which is chemically inert to mobile phase 24, but provides a relatively hard surface on which gasket 112 and membrane 144 can rest. The sample to be separated is then spotted on sample area 22 of plate 12.

Figure 6:
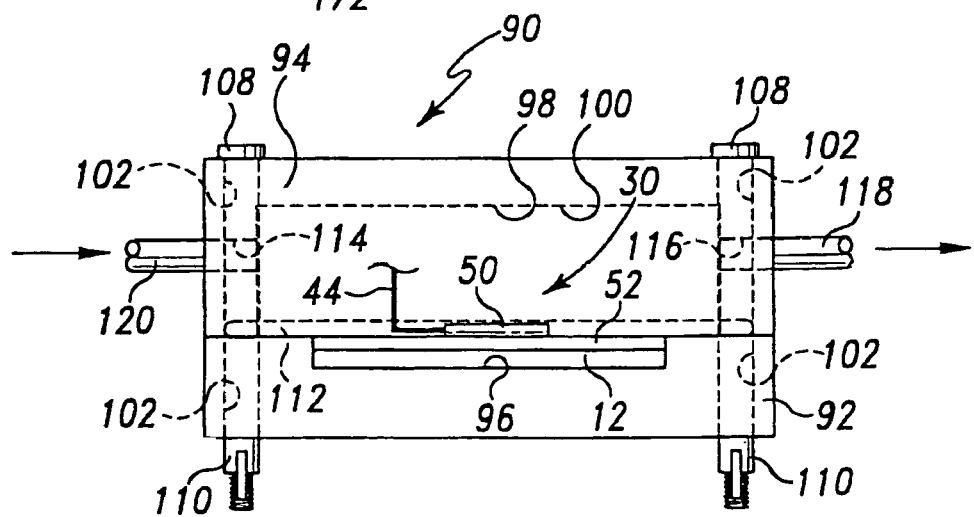
FIG. 6 is an end elevational view of the chromatography arrangement shown in FIG. 4 as viewed in the direction of line 6-6.

Plate 12 is then positioned relative to first member 92 so that plate 12 is located within seat area 96 (see FIG. 6). As more clearly shown in FIG. 7, a pliable membrane 144 is positioned in contact with chromatographic bed 16 so that chromatographic bed 16 is interposed between membrane 144 and support 14. Membrane 144 can be made out of any appropriate material which has a low electrical conductivity and a relatively high thermal conductivity. For example, the membrane 144 used in the present invention can be made out of a 1/16 inch thick sheet of polytetrafluoroethylene (Teflon). In addition, membrane 144 can include a sheet of mylar attached to the surface of the Teflon sheet which faces toward sealed cavity 100. Moreover, membrane 144 can include a sheet of Kel-F CTFE attached to the surface of the Teflon sheet which faces toward sealed cavity 100. Kel-F CTFE is commercially available from McMaster-Carr Supply Company, located in Chicago, Ill. Yet another material which can be incorporated into membrane 144 is AN 90 aluminum nitride ceramic which is commercially available from MarkeTech located in Port Townsend, Wash. However, as with mylar if AN 90 aluminum nitride ceramic is incorporated into membrane 144 the Teflon sheet must contact the chromatographic bed. Furthermore, membrane 144 can include any sandwich combination of the above mentioned materials as long as the Kel-F CTFE or Teflon sheet is in contact with the chromatographic bed 16.

Once plate 12 is positioned within seat area 96, and membrane 144 is placed into contact with chromatographic bed 16, second member 94 is positioned relative to first member 92 so that the holes 102 defined in both members are aligned. A fastener 108 is then inserted through each hole 108 and a nut 110 is meshingly engaged with each fastener 108. Positioning and securing second member 94 to first member 92 in the above described manner results in (i) sealed cavity 100 being defined between first member 92 and second member 94, (ii) gasket 112 being positioned in contact with membrane 144 and located over sealant 148, and (iii) a portion 166 of chromatographic bed 16 being located within sealed cavity 100.

One end of a metallic conduit 118 is then placed in fluid communication with an exit orifice 116 defined in second member 94 as shown in FIG. 4. The other end of conduit 118 is placed in fluid communication with a pump 122. One end of another metallic conduit 120 is also placed in fluid communication with pump 122 while the other end of conduit 120 is placed in fluid communication with an entrance orifice 114 defined in second member 94. Furthermore, a coiled portion 138 of conduit 120 is located within cooling unit 132. Coiled portion 138 is in contact with a cooling fluid 136 contained within cooling unit 132.

Temperature sensor 126 is positioned within sealed cavity 100 such that temperature sensor 126 can measure the temperature of a fluid being advanced through sealed cavity 100. Note that temperature sensor 126 can also be positioned within conduit 118 adjacent to exit orifice 116. Temperature sensor 126 is electrically coupled to temperature control unit 128 by an electrical line 130. Temperature control unit 128 is electrically coupled to cooling unit 132 by electrical line 134. It should be understood that temperature sensor 126 detects the temperature of a fluid being advanced through sealed cavity 100 and communicates the temperature data to temperature control unit 128. Temperature control unit 128 then controls the operation of cooling unit 132 based upon the data received from temperature sensor 126. For example, temperature control unit 128 may cause cooling unit 132 to cool or warm the cooling liquid 136 within cooling unit 132 depending upon the data received from temperature sensor 126. Therefore, it should be appreciated that temperature sensor 126, cooling unit 132, and temperature control unit 128 cooperate in a well known manner to maintain any fluid being advanced through conduit 120, and therefore sealed cavity 100, within a predetermined temperature range.

Container 90, with plate 12 contained therein, is then positioned relative to tank 73 so that end 20 of plate 12 is located below surface 26 of mobile phase 24. However, sample area 22 is located within sealed cavity 100 above surface 26 of mobile phase 24. Cathode 30 and anode 28 are electrically coupled to power source 40 via electrical wires 44 and 42 as previously discussed. In addition, anode 28 is positioned in contact with mobile phase 24 as shown in FIG. 4. Moreover, cathode 30 is positioned in contact with cathode portion 170 of plate 12 which is located outside of sealed cavity 100 (see FIG. 7). In addition, wick 75 is interposed between platinum foil 52 and chromatographic bed 16 as previously discussed. An electrical potential is then generated between cathode 30 and anode 28 with power source 40 to develop plate 12 in a manner substantially identical to that described above in reference to arrangements 10 and 37.

Once plate 12 begins to develop, pump 122 is actuated so that a fluid 168 is advanced under pressure into sealed cavity 100 in the directions indicated by arrows 140 (see FIG. 4). Note that (i) baffles 124 attached to an inside wall of sealed cavity 100 cause fluid 168 to travel through sealed cavity in a serpentine fashion and (ii) membrane 144 prevents fluid 168 from coming into contact with chromatographic bed 16. It should be understood that fluid 168 is advanced into sealed cavity 100 so that the pressure within sealed cavity 100 is greater than the pressure outside of sealed cavity 100. For example, pressure within sealed cavity 100 can be in the range of about 3 to 50 atmospheres. Placing sealed cavity 100 under the aforementioned pressure also subjects the portion 166 of the chromatographic bed 16 located within sealed cavity 100 under the same pressure. Having portion 166 of the chromatographic bed 16 under pressure during the development of plate 12 is an important aspect of the present invention since it substantially enhances the separation efficiency of arrangement 88. Furthermore, advancing fluid 168 into sealed cavity 100 under pressure places fluid 168 and plate 12 in a heat exchange relationship with chromatographic bed 16 such that temperature control unit 128, in cooperation with cooling unit 132, can maintain the temperature of plate 12 within a predetermined range. In particular, maintaining plate 12 within a predetermined temperature range prevents ohmic over heating of plate 12 which can reduce the separation efficiency of arrangement 88.

The fluid 168 being advanced through sealed cavity 100 is preferably a chemically inert, liquid which has a very low electrical conductivity. Such a liquid is commercially available from the 3M Corporation, located in Minneapolis, Minn., as Fluorinert or FC-77. In addition, megohm quality water could be used.

Once plate 12 develops, container 90 can be disassembled by removing fasteners 108 and separating first element 92 from second element 94. After separating first element 92 from second element 94 plate 12 can be recovered.

Figure 8:
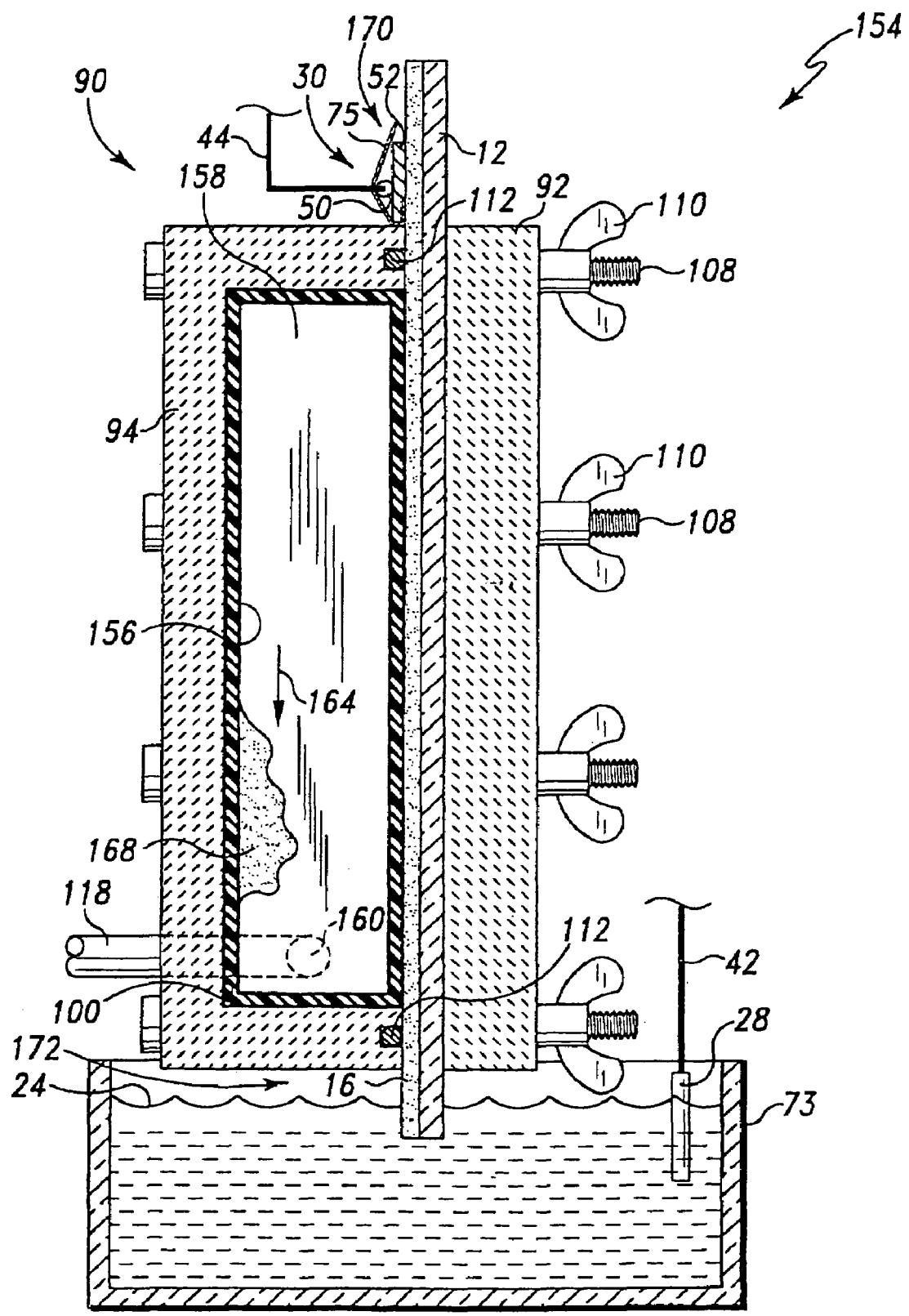
FIG. 8 is a cross sectional view of a chromatography arrangement similar to the one shown in FIG. 5, but showing a bladder disposed within the sealed cavity of the container.

Referring now to FIG. 8, there is shown an arrangement 154 which is substantially similar to arrangement 88 and therefore a detailed description of all the elements of arrangement 154 will not be provided herein. It should be understood that arrangement 154 functions in substantially the same way, and has the same advantages, as discussed above in reference to arrangement 88. In particular, it should be understood that arrangement 154 also drives the mobile phase 24 through the chromatographic bed 16 of plate 12 utilizing an electrical potential generated between first electrode 28 and second electrode 30. However, the container 90 of arrangement 154 has a bladder 156 positioned within sealed cavity 100 rather than a number of baffles 124 and membrane 144.

Bladder 156 defines a void 158. Additionally, bladder 156 has an exit aperture 160 defined therein which is in fluid communication with conduit 118. Bladder 156 also has an entrance aperture (not shown) which is in fluid communication with conduit 120 (see FIG. 4). When developing plate 12 with arrangement 154, pump 122 advances fluid 168 under pressure into void 158 which causes (i) the pressure within sealed cavity 100 to be greater than the pressure outside of sealed cavity 100 and (ii) bladder 156 to be urged into contact with chromatographic bed 16 of plate 12. Urging bladder 156 into contact with chromatographic bed 16 places chromatographic bed 16 under pressure so as to substantially increase the separation efficiency of arrangement 154. Furthermore, urging bladder 156 against plate 12 places fluid 168 in void 158 in a heat exchange relationship with chromatographic bed 16 such that temperature control unit 128, in cooperation with cooling unit 132, can maintain the temperature of plate 12 within a predetermined range.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected. For example, while plate 12 is shown being orientated in a vertical position herein other orientations are contemplated, e.g. horizontal. Furthermore, the above described invention can be used with bidirectional chromatography in which the mobile phase is advanced in two opposite directions. This arrangement involves two parallel cathodes with an anode being centrally located relative to the cathodes. In addition, nonaqueous mobile phases can be utilized with an appropriate chromatographic bed. Moreover, the cathode can be positioned within sealed cavity 100. Furthermore, it should be understood that the present invention lends itself to simultaneously separating multiple samples at a time on a single plate 12. For example, 80 samples could be separated on a 40 cm wide plate 12.

What is claimed is:

1. A method of performing chromatography with a chromatographic bed having a stationary phase, comprising the steps of:
   positioning the chromatographic bed and the stationary phase within a sealed cavity;
   placing the stationary phase in contact with a liquid mobile phase while the stationary phase is positioned within the sealed cavity;
   advancing a fluid into the sealed cavity so that pressure within the sealed cavity is greater than the pressure outside of the sealed cavity;
   placing a first electrode in contact with the liquid mobile phase;
   placing a second electrode in contact with the chromatographic bed; and creating an electrical potential between the first electrode and the second electrode so as to cause the liquid mobile phase to be advanced through the chromatographic bed positioned within the sealed cavity.

2. The method of claim 1, wherein:
said first electrode includes an anode, and
said second electrode includes a cathode.

3. The method of claim 2, wherein:
the stationary phase includes a thin layer chromatography plate having a cathode portion and an anode portion,
the mobile phase includes a liquid,
the anode portion of the thin layer chromatography plate is in contact with the liquid when the stationary phase is located within the sealed cavity,
the cathode is in contact with the cathode portion of the thin layer chromatography plate,
the anode is in contact with the liquid of the mobile phase, and
creating an electrical potential between the cathode and the anode causes the liquid of the mobile phase to migrate through the chromatographic bed in a direction away from the anode portion and toward the cathode portion.

4. The method of claim 3, wherein:
the cathode includes a platinum wire attached to a piece of platinum foil, and the platinum foil is positioned in contact with the cathode portion of the thin layer chromatography plate.

5. The method of claim 1, wherein:
the advancing step includes the step of placing a bladder having a void defined therein within the sealed cavity and advancing the fluid into the void so that the bladder is urged against the stationary phase.

6. The method of claim 5, wherein:
the fluid advanced into the void of the bladder includes a liquid, and
creating the electrical potential step includes the step of placing the liquid in a heat exchange relationship with the stationary phase so that the liquid cools the stationary phase.

7. The method of claim 1, further comprising the step of:
positioning an absorbing element in contact with said stationary phase so that the absorbing element absorbs the liquid when the electrical potential is created between the first electrode and the second electrode.

8. A method of performing chromatography, comprising:
(a) exerting a pressure which is greater than atmospheric pressure against a stationary phase which is supported by a plate;
(b) placing the stationary phase in contact with a liquid mobile phase; and
(c) creating an electrical potential across the stationary phase with a first electrode and a second electrode so as to cause the liquid mobile phase to be advanced across the stationary phase.

9. The method of claim 8, further comprising:
(a) placing the stationary phase in thermal communication with a cooling device; and
(b) cooling the stationary phase with the cooling device.

10. A method of performing chromatography, comprising:
(a) placing a stationary phase supported by a plate in contact with a liquid mobile phase;
(b) creating an electrical potential across the stationary phase with a first electrode and a second electrode so as to cause the liquid mobile phase to be advanced across the stationary phase; and
(c) cooling the stationary phase with a cooling device placed in thermal communication with the stationary phase as the liquid mobile phase is advanced across the stationary phase.

11. A method of performing chromatography, comprising:
(a) placing a stationary phase which is supported by a plate in contact with a liquid mobile phase;
(b) creating an electrical potential across the stationary phase with a first electrode and a second electrode so as to cause the liquid mobile phase to be advanced across the stationary phase; and
(c) maintaining the stationary phase within a predetermined temperature range with a temperature control device placed in thermal communication with the stationary phase as the liquid mobile phase is advanced across the stationary phase.

12. The method of claim 11, further comprising:
(a) exerting a pressure which is greater than atmospheric pressure against the stationary phase.

* * * * *